US007033751B2

(12) United States Patent
Lin et al.

(10) Patent No.: US 7,033,751 B2
(45) Date of Patent: Apr. 25, 2006

(54) ANTIGENIC FRAGMENT OF HUMAN T-LYMPHOTROPIC VIRUS

(75) Inventors: Hsin-Yu Lin, Banchiau (TW); Ching-Long Hwong, Kaohsiung (TW)

(73) Assignee: Development Center for Biotechnology, Taipei (TW)

( * ) Notice: Subject to any disclaimer, the term of this patent is extended or adjusted under 35 U.S.C. 154(b) by 134 days.

(21) Appl. No.: 10/423,156

(22) Filed: Apr. 25, 2003

(65) Prior Publication Data

US 2004/0116662 A1    Jun. 17, 2004

(30) Foreign Application Priority Data

Dec. 12, 2002    (TW)    ............... 91135980 A

(51) Int. Cl.
  C12Q 1/70      (2006.01)
  C12N 15/46     (2006.01)
  C12N 15/62     (2006.01)
  C07K 14/15     (2006.01)
  C07K 19/00     (2006.01)

(52) U.S. Cl. .............. 435/5; 435/320.1; 435/69.3; 530/350; 536/23.2; 536/23.4; 536/23.72; 424/187.1; 424/192.1; 424/207.1

(58) Field of Classification Search .......... 530/350; 536/23.72, 23.4, 23.2; 435/320.1, 69.3, 5; 424/188.1, 187.1, 192.1, 207.1
See application file for complete search history.

(56) References Cited

U.S. PATENT DOCUMENTS

| 5,310,876 A * | 5/1994 | Bayer et al. ............... 530/350 |
| 5,643,174 A | 7/1997 | Yamamoto et al. |
| 6,406,841 B1 * | 6/2002 | Lee et al. ..................... 435/5 |

FOREIGN PATENT DOCUMENTS

| EP | 0 424 748 | 5/1991 |
| EP | 0424748 | * 5/1991 |
| EP | 0781848 | * 12/1996 |
| JP | 2000-078973 | * 3/2000 |
| WO | WO 9639630 | 12/1996 |

OTHER PUBLICATIONS

Abbott Murex. Murex HTLV I+II advertisement. [Retrieved on Sep. 30, 2004] from the Internet <URL: http://abbott-murex.com/products/go80.htm>.*
Lal, R.B. Journal of Acquired Immune Deficiency Syndromes and Human Retrovirology 13 (Suppl1):S170-S178, 1996.*
Marin et al., "Chimeric Synthetic Peptides Containing Two Immunodominant Epitopes from the Envelope gp46 and the Transmembrane gp21 Glycoproteins of HTLV-1 Virus", Biochemical and Biophysical Research Communications 289:1-6, 2001.
Marin et al., "Chimeric Synthetic Peptides from the Envelope (gp46) and the Transmembrane (gp21) Glycoproteins for the Detection of Antibodies to Human T-Cell Leukemia Virus Type II", Biochemical and Biophysical Research Communications 289:7-12, 2001.
Gray et al. "Envelope Gene Sequence of HTLV-1 Isolate MT-2 and its Comparison with Other HTLV-1 Isolates". Virology 177:391-395, 1990.
Horal et al. "Identification of type-specific linear epitopes in the glycoproteins gp46 and gp21 of human T-cell leukemia viruses type I and type II using synthetic peptides". Proc. Natl. Acad. Sci. USA 88(13):5754-5758, Jul. 1, 1991.
Palker et al. "Mapping of immunogenic regions of human T cell leukemia virus type I (HTLV-1) gp46 and gp21 envelope glycoproteins with env-coded synthetic peptides and a monoclonal antibody to gp46". Journal of Immunology 142(3):971-978, Feb. 1, 1989.
Tallet et al. "One-step chromatographic purification procedure of a His-tag recombinant carboxyl half part of the HTLV-1 surface envelope glycoprotein overexpressed in *Escherichia coli* as a secreted form". Journal of Chromatography B 753:17-22, 2001.
Kitze et al. "Human CD+ T lymphocytes recognize a highly conserved epitope of human T lymphotrophic virus type I (HTLV-1)j env gp21 restricted by HLA DRB1*0101". Clin Exp. Immunol. 111:278-285, 1998.
Varma et al. "Enhanced Specificity of Truncated Transmembrane Protein for Serologic Confirmation of Human T-Cell Lymphotropic Virus Type 1 (HTLV-1) and HTLV-2 Infections by Western Blot (Immunoblot) Assay Containing Recombinant Envelope Glycoproteins". Journal of Clinical Microbiology 33(12):3239-3244, 1995.
Wang et al. "Molecular Cloning, Expression, and Biological Characterization of an HTLV-II Envelope Glucoprotein: HIV-1 Expression Is Permissive for HTLV-II-Induced Cell Fusion". Aids Research and human Retroviruses 9(9):849-860, 1993.
Yamano et al. "Preferential recognition of synthetic peptides from HTLV-I gp21 envelope protein by HLA-DRN1 alleles associated with HAM/TSP (HTLV-I-associated myelopathy/tropical spactic paraparesis)". Journal of Neuroimmunology 76:50-60, 1997.

(Continued)

Primary Examiner—Mary E. Mosher
(74) Attorney, Agent, or Firm—Fish & Richardson P.C.

(57) ABSTRACT

Antigenic fragments of human T-lymphotropic virus (HTLV), their fusion proteins with glutathione S-tranferase (GST) or thioredoxin (Thio), and a process for producing the fusion proteins thereof. The antigenic fragment of HTLV comprises the amino acid sequence of SEQ ID Nos: 3 or 4.

12 Claims, 8 Drawing Sheets

OTHER PUBLICATIONS

Database www.uniprot.org—Accession No. Q9WJZ9. Nov. 1, 1999.
Database www.uniprot.org—Accession No. Q82316. Nov. 1, 1996.
Database www.uniprot.org—Accession No. Q82317. Nov. 1, 1996.
Database www.uniprot.org—Accession No. 82315. Nov. 1, 1996.
Database www.uniprot.org—Accession No. Q9JFQ4. Oct. 1, 2000.
Database www.uniprot.org—Accession No. Q80806. Nov. 1, 1996.

* cited by examiner

HTLV-I gp21

ATGGGTGCAGGGCGTTGCTGGGTATCACCGGCTCCATGTCCCTGGCATCC
GGTAAATCTCTGCTGCACGAAGTTGACAAAGACATCTCCCAGCTGACTCAG
GCAATCGTTAAAACCACAAAAACCTGCTGAAAATCGGCAGTACGCTGC
ACAGAACCGTCGTGGCCTGGACCTGCTGTTCTGGGAACAGGGTGGCCTGT
GCAAAGCACTGCAGGAACAGTGCTGTTCCTGAACATCACTAACTCCCACG
TTTCTATCCTGAACTGGGACCTGTCTCAGTGGGCTCGTGAGGCGCTG
GGGGCTGAACTGGGACCTGTCTCAGTGGGCTCGTGAGGCGCTG
CAGACTGGTATCACCCTGCTGCTGTTATCCTGGCAGGT
CCGTGCATCCTGCGTCAGCTGCACCTGCTCGTACGTTACCCG
CACTACTCTCTGATCAAACCGGAATCTCCCTGTAA

FIG. 1A

HTLV-II gp21

ATGGCCGGGACACAGGTATCGCTGGGGAGTAACAGGCTCCCTATCTCTAGCT
TCCAGTAAAGCCTTCTCTCGAGGTGACAAAGATATCTCCCACCTTACCC
AGGCCATAGTCAAAATCATCAAAACATCCGGGTGCACAATATGCAG
CCCAGAATAGACGAGGATTAGACCTCCTATTCTGGGAACAAGGGGTTGT
GCAAAGCCATACAGGAGCAATGTGCTCCTCAATATCAGTAACACTCATGT
ATCCGTCCCAAGAACGGCCCCTCTGAAAAGCGTGTCATCACCGGTTG
GGGACTAAACTGGGATCTTGGTCTCCCAGTGGCACGAGAAGCCCTCC
AGACAGGCATAACCATTCTCACCCTACTCCTCCTTGTCATATGTTTGGCCC
CTGCATCCCTCCGCAAATCCAAGCCCTTCCGCAGCGGGTTACAAAACCGACA
TAG CCAGTATGCCCTTATCAACCAAGAGACCATGCTATAA

SEQUENCE LISTING

<160> NUMBER OF SEQ ID NOS: 60

<210> SEQ ID NO 1
<211> LENGTH: 163
<212> TYPE: PRT
<213> ORGANISM: Homo sapiens

<400> SEQUENCE: 1

```
Met Gly Ala Gly Val Ala Gly Arg Ile Thr Gly Ser Met Ser Leu Ala
1               5                   10                  15

Ser Gly Lys Ser Leu Leu His Glu Val Asp Lys Asp Ile Ser Gln Leu
            20                  25                  30

Thr Gln Ala Ile Val Lys Asn His Lys Asn Leu Leu Lys Ile Ala Gln
        35                  40                  45

Tyr Ala Ala Gln Asn Arg Arg Gly Leu Asp Leu Leu Phe Trp Glu Gln
    50                  55                  60

Gly Gly Leu Cys Lys Ala Leu Gln Glu Gln Cys Cys Phe Leu Asn Ile
65                  70                  75                  80

Thr Asn Ser His Val Ser Ile Leu Gln Glu Arg Pro Pro Leu Glu Asn
                85                  90                  95

Arg Val Leu Thr Gly Trp Gly Leu Asn Trp Asp Leu Gly Leu Ser Gln
            100                 105                 110

Trp Ala Arg Glu Ala Leu Gln Thr Gly Ile Thr Leu Val Ala Leu Leu
        115                 120                 125

Leu Leu Val Ile Leu Ala Gly Pro Cys Ile Leu Arg Gln Leu Arg His
    130                 135                 140

Leu Pro Ser Arg Val Arg Tyr Pro His Tyr Ser Leu Ile Asn Pro Glu
145                 150                 155                 160

Ser Ser Leu
```

<210> SEQ ID NO 2
<211> LENGTH: 166
<212> TYPE: PRT
<213> ORGANISM: Homo sapiens

<400> SEQUENCE: 2

```
Met Ala Gly Thr Gly Ile Ala Gly Gly Val Thr Gly Ser Leu Ser Leu
1               5                   10                  15
```

```
Ala Ser Ser Lys Ser Leu Leu Phe Glu Val Asp Lys Asp Ile Ser His
             20                  25                  30

Leu Thr Gln Ala Ile Val Lys Asn His Gln Asn Ile Leu Arg Val Ala
         35                  40                  45

Gln Tyr Ala Ala Gln Asn Arg Arg Gly Leu Asp Leu Leu Phe Trp Glu
     50                  55                  60

Gln Gly Gly Leu Cys Lys Ala Ile Gln Glu Gln Cys Cys Phe Leu Asn
 65                  70                  75                  80

Ile Ser Asn Thr His Val Ser Val Leu Gln Glu Arg Pro Pro Leu Glu
                 85                  90                  95

Lys Arg Val Ile Thr Gly Trp Gly Leu Asn Trp Asp Leu Gly Leu Ser
             100                 105                 110

Gln Trp Ala Arg Glu Ala Leu Gln Thr Gly Ile Thr Ile Leu Ala Leu
         115                 120                 125

Leu Leu Leu Val Ile Leu Phe Gly Pro Cys Ile Leu Arg Gln Ile Gln
     130                 135                 140

Ala Leu Pro Gln Arg Leu Gln Asn Arg His Asn Gln Tyr Ser Leu Ile
145                 150                 155                 160

Asn Pro Glu Thr Met Leu
                 165

<210> SEQ ID NO 3
<211> LENGTH: 89
<212> TYPE: PRT
<213> ORGANISM: Homo sapiens

<400> SEQUENCE: 3

Ala Ser Gly Lys Ser Leu Leu His Glu Val Asp Lys Asp Ile Ser Gln
 1               5                  10                  15

Leu Thr Gln Ala Ile Val Lys Asn His Lys Asn Leu Leu Lys Ile Ala
             20                  25                  30

Gln Tyr Ala Ala Gln Asn Arg Arg Gly Leu Asp Leu Leu Phe Trp Glu
         35                  40                  45

Gln Gly Gly Leu Cys Lys Ala Leu Gln Glu Gln Cys Cys Phe Leu Asn
     50                  55                  60

Ile Thr Asn Ser His Val Ser Ile Leu Gln Glu Arg Pro Pro Leu Glu
 65                  70                  75                  80

Asn Arg Val Leu Thr Gly Trp Gly Leu
                 85

<210> SEQ ID NO 4
<211> LENGTH: 89
<212> TYPE: PRT
<213> ORGANISM: Homo sapiens

<400> SEQUENCE: 4

Ala Ser Ser Lys Ser Leu Leu Phe Glu Val Asp Lys Asp Ile Ser His
 1               5                  10                  15

Leu Thr Gln Ala Ile Val Lys Asn His Gln Asn Ile Leu Arg Val Ala
             20                  25                  30

Gln Tyr Ala Ala Gln Asn Arg Arg Gly Leu Asp Leu Leu Phe Trp Glu
         35                  40                  45

Gln Gly Gly Leu Cys Lys Ala Ile Gln Glu Gln Cys Cys Phe Leu Asn
     50                  55                  60
```

```
Ile Ser Asn Thr His Val Ser Val Leu Gln Glu Arg Pro Pro Leu Glu
 65                  70                  75                  80

Lys Arg Val Ile Thr Gly Trp Gly Leu
                 85
```

<210> SEQ ID NO 5
<211> LENGTH: 335
<212> TYPE: PRT
<213> ORGANISM: Artificial Sequence
<220> FEATURE:
<223> OTHER INFORMATION: Shynthetically generated peptide

<400> SEQUENCE: 5

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Lys Tyr Glu Glu His Leu
                 20                  25                  30

Tyr Glu Arg Asp Glu Gly Asp Lys Trp Arg Asn Lys Lys Phe Glu Leu
                 35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
                130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Asp His Pro Pro Lys Ser Asp Leu Val Pro Arg
                210                 215                 220

Gly Ser Pro Gly Ile Ser Gly Gly Gly Gly Ile Leu Asp Ser Met
225                 230                 235                 240

Gly Ala Ser Gly Lys Ser Leu Leu His Glu Val Asp Lys Asp Ile Ser
                245                 250                 255

Gln Leu Thr Gln Ala Ile Val Lys Asn His Lys Asn Leu Leu Lys Ile
                260                 265                 270

Ala Gln Tyr Ala Ala Gln Asn Arg Arg Gly Leu Asp Leu Leu Phe Trp
                275                 280                 285

Glu Gln Gly Gly Leu Cys Lys Ala Leu Gln Glu Gln Cys Cys Phe Leu
                290                 295                 300

Asn Ile Thr Asn Ser His Val Ser Ile Leu Gln Glu Arg Pro Pro Leu
305                 310                 315                 320

Glu Asn Arg Val Leu Thr Gly Trp Gly Leu Lys Leu Asn Ser Ser
                325                 330                 335
```

<210> SEQ ID NO 6
<211> LENGTH: 327
<212> TYPE: PRT
<213> ORGANISM: Artificial Sequence
<220> FEATURE:
<223> OTHER INFORMATION: Shynthetically generated peptide

<400> SEQUENCE: 6

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
 50                  55                  60

Leu Thr Gly Leu Ser Met Ala Ile Ile Arg Tyr Ile Ala Asp Lys His
 65                  70                  75                  80

Asn Met Leu Gly Gly Cys Pro Lys Glu Arg Ala Glu Ile Ser Met Leu
                 85                  90                  95

Glu Gly Ala Val Leu Asp Ile Arg Tyr Gly Val Ser Arg Ile Ala Tyr
            100                 105                 110

Ser Lys Asp Phe Glu Thr Leu Lys Val Asp Phe Leu Ser Lys Leu Pro
        115                 120                 125

Glu Met Leu Lys Met Phe Glu Ala Ser Arg Leu Cys His Lys Thr Tyr
130                 135                 140

Leu Asn Gly Asp His Val Thr His Pro Asp Phe Met Leu Tyr Asp Ala
145                 150                 155                 160

Leu Ala Ser Val Val Leu Tyr Met Ala Ser Pro Met Cys Leu Asp Ala
                165                 170                 175

Phe Pro Lys Leu Val Cys Phe Lys Lys Arg Ile Glu Ala Ile Pro Gln
            180                 185                 190

Ile Asp Lys Tyr Leu Lys Ser Ser Lys Tyr Ile Ala Trp Pro Leu Gln
        195                 200                 205

Gly Trp Gln Ala Thr Phe Gly Gly Gly Asp His Pro Pro Lys Ser Asp
    210                 215                 220

Leu Val Pro Arg Gly Ser Ala Ser Ser Lys Ser Leu Leu Phe Glu Val
225                 230                 235                 240

Asp Lys Ala Ser Ile Ser His Leu Thr Gln Ala Ile Val Lys Asn His
                245                 250                 255

Gln Asn Ile Leu Arg Val Ala Gln Tyr Ala Ala Gln Asn Arg Arg Gly
            260                 265                 270

Leu Asp Leu Leu Phe Trp Glu Gln Gly Gly Leu Cys Lys Ala Ile Gln
        275                 280                 285

Glu Gln Cys Cys Phe Leu Asn Ile Ser Ala Ser Thr His Val Ser Val
    290                 295                 300

Leu Gln Glu Arg Pro Pro Leu Glu Lys Arg Val Ile Thr Gly Trp Gly
305                 310                 315                 320

Leu Lys Leu Ala Ser Ser Ser
                325
```

<210> SEQ ID NO 7
<211> LENGTH: 252
<212> TYPE: PRT
<213> ORGANISM: Artificial Sequence
<220> FEATURE:
<223> OTHER INFORMATION: Shynthetically generated peptide

```
<400> SEQUENCE: 7

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala His Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp His Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly Asp Asp Asp Lys Val Pro Met Gly Ser Ser His His His His
            115                 120                 125

His His Ser Ser Gly Leu Val Pro Arg Gly Ser His Met Ala Ser
        130                 135                 140

Gly Lys Ser Leu Leu His Glu Val Asp Lys Asp Ile Ser Gln Leu Thr
145                 150                 155                 160

Gln Ala Ile Val Lys Asn His Lys Asn Leu Leu Lys Ile Ala Gln Tyr
                165                 170                 175

Ala Ala Gln Asn Arg Arg Gly Leu Asp Leu Leu Phe Trp Glu Gln Gly
            180                 185                 190

Gly Leu Cys Lys Ala Leu Gln Glu Gln Cys Cys Phe Leu Asn Ile Thr
        195                 200                 205

Asn Ser His Val Ser Ile Leu Gln Glu Arg Pro Pro Leu Glu Asn Arg
    210                 215                 220

Val Leu Thr Gly Trp Gly Leu Leu Glu Ile Phe Glu Phe Arg Gly Arg
225                 230                 235                 240

Arg Pro Leu Glu Ser Thr Cys Ser Asn Arg Thr Gly
                245                 250

<210> SEQ ID NO 8
<211> LENGTH: 252
<212> TYPE: PRT
<213> ORGANISM: Artificial Sequence
<220> FEATURE:
<223> OTHER INFORMATION: Shynthetically generated peptide

<400> SEQUENCE: 8

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala His Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp His Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95
```

```
Lys Gly Gln Leu Lys Glu Phe Leu Asp Ala Asn Leu Ala Gly Ser Gly
            100                 105                 110

Ser Gly Asp Asp Asp Lys Val Pro Met Gly Ser Ser His His His
        115                 120                 125

His His His Ser Ser Gly Leu Val Pro Arg Gly Ser Met Ala Ser
    130                 135                 140

Ser Lys Ser Leu Leu Phe Glu Val Asp Lys Asp Ile Ser His Leu Thr
145                 150                 155                 160

Gln Ala Ile Val Lys Asn His Gln Asn Ile Leu Arg Val Ala Gln Tyr
                165                 170                 175

Ala Ala Gln Asn Arg Arg Gly Leu Asp Leu Leu Phe Trp Glu Gln Gly
                180                 185                 190

Gly Leu Cys Lys Ala Ile Gln Glu Gln Cys Cys Phe Leu Asn Ile Ser
            195                 200                 205

Asn Thr His Val Ser Val Leu Gln Glu Arg Pro Pro Leu Glu Lys Arg
    210                 215                 220

Val Ile Thr Gly Trp Gly Leu Leu Glu Ile Phe Glu Phe Arg Gly Arg
225                 230                 235                 240

Arg Pro Leu Glu Ser Thr Cys Ser Asn Arg Thr Gly
                245                 250
```

```
<210> SEQ ID NO 9
<211> LENGTH: 492
<212> TYPE: DNA
<213> ORGANISM: Artificial Sequence
<220> FEATURE:
<223> OTHER INFORMATION: Synthetically generated oligonucleotide

<400> SEQUENCE: 9
atgggtgcag gcgttgctgg cggtatcacc ggctccatgt ccctggcatc cggtaaatct      60
ctgctgcacg aagttgacaa agacatctcc cagctgactc aggcaatcgt taaaaaccac     120
aaaaacctgc tgaaaatcgc gcagtacgct gcacagaacc gtcgtggcct ggacctgctg     180
ttctgggaac agggtggcct gtgcaaagca ctgcaggaac agtgctgttt cctgaacatc     240
actaactccc acgtttctat cctgcaggaa cgtccgccgc tggaaaaccg tgtactgact     300
ggctggggcc tgaactggga cctgggcctg tctcagtggg ctcgtgaggc gctgcagact     360
ggtatcaccc tggttgcgct gctgctgctg gttatcctgg caggtccgtg catcctgcgt     420
cagctgcgtc acctgccgtc tcgtgtacgt tacccgcact actctctgat caaaccggaa     480
tcttccctgt aa                                                         492
```

```
<210> SEQ ID NO 10
<211> LENGTH: 40
<212> TYPE: DNA
<213> ORGANISM: Artificial Sequence
<220> FEATURE:
<223> OTHER INFORMATION: Primer

<400> SEQUENCE: 10
cgcatatggg tgcaggcgtt gctggcggta tcaccggctc                            40
```

```
<210> SEQ ID NO 11
<211> LENGTH: 40
<212> TYPE: DNA
<213> ORGANISM: Artificial Sequence
<220> FEATURE:
<223> OTHER INFORMATION: Primer
```

-continued

<400> SEQUENCE: 11
tggcatccgg taaatctctg ctgcacgaag ttgacaaaga                40

<210> SEQ ID NO 12
<211> LENGTH: 40
<212> TYPE: DNA
<213> ORGANISM: Artificial Sequence
<220> FEATURE:
<223> OTHER INFORMATION: Primer

<400> SEQUENCE: 12
agctgactca ggcaatcgtt aaaaaccaca aaaacctgct                40

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
cgcagtacgc tgcacagaac cgtcgtggcc tggacctgct                40

<210> SEQ ID NO 14
<211> LENGTH: 40
<212> TYPE: DNA
<213> ORGANISM: Artificial Sequence
<220> FEATURE:
<223> OTHER INFORMATION: Primer

<400> SEQUENCE: 14
aacagggtgg cctgtgcaaa gcactgcagg aacagtgctg                40

<210> SEQ ID NO 15
<211> LENGTH: 40
<212> TYPE: DNA
<213> ORGANISM: Artificial Sequence
<220> FEATURE:
<223> OTHER INFORMATION: Primer

<400> SEQUENCE: 15
acatcactaa ctcccacgtt tctatcctgc aggaacgtcc                40

<210> SEQ ID NO 16
<211> LENGTH: 40
<212> TYPE: DNA
<213> ORGANISM: Artificial Sequence
<220> FEATURE:
<223> OTHER INFORMATION: Primer

<400> SEQUENCE: 16
aaaaccgtgt actgactggc tggggcctga actgggacct                40

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
ctcagtgggc tcgtgaggcg ctgcagactg gtatcaccct                40

```
<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
tgctgctgct ggttatcctg gcaggtccgt gcatcctgcg                           40

<210> SEQ ID NO 19
<211> LENGTH: 40
<212> TYPE: DNA
<213> ORGANISM: Artificial Sequence
<220> FEATURE:
<223> OTHER INFORMATION: Primer

<400> SEQUENCE: 19
gtcacctgcc gtctcgtgta cgttacccgc actactctct                           40

<210> SEQ ID NO 20
<211> LENGTH: 49
<212> TYPE: DNA
<213> ORGANISM: Artificial Sequence
<220> FEATURE:
<223> OTHER INFORMATION: Primer

<400> SEQUENCE: 20
cgctcgagtt acagggaaga ttccggtttg atcagagagt agtgcgggt                 49

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
cgagacggca ggtgacgcag ctgacgcagg atgcacggac                           40

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
ataaccagca gcagcagcgc aaccagggtg ataccagtct                           40

<210> SEQ ID NO 23
<211> LENGTH: 40
<212> TYPE: DNA
<213> ORGANISM: Artificial Sequence
<220> FEATURE:
<223> OTHER INFORMATION: Primer

<400> SEQUENCE: 23
tcacgagccc actgagacag gcccaggtcc cagttcaggc                           40

<210> SEQ ID NO 24
<211> LENGTH: 40
<212> TYPE: DNA
<213> ORGANISM: Artificial Sequence
<220> FEATURE:
<223> OTHER INFORMATION: Primer
```

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 24
gtcagtacac ggttttccag cggcggacgt tcctgcagga                40

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 25
tgggagttag tgatgttcag gaaacagcac tgttcctgca                40

<210> SEQ ID NO 26
<211> LENGTH: 40
<212> TYPE: DNA
<213> ORGANISM: Artificial Sequence
<220> FEATURE:
<223> OTHER INFORMATION: Primer

<400> SEQUENCE: 26
cacaggccac cctgttccca gaacagcagg tccaggccac                40

<210> SEQ ID NO 27
<211> LENGTH: 40
<212> TYPE: DNA
<213> ORGANISM: Artificial Sequence
<220> FEATURE:
<223> OTHER INFORMATION: Primer

<400> SEQUENCE: 27
tgtgcagcgt actgcgcgat tttcagcagg tttttgtggt                40

<210> SEQ ID NO 28
<211> LENGTH: 40
<212> TYPE: DNA
<213> ORGANISM: Artificial Sequence
<220> FEATURE:
<223> OTHER INFORMATION: Primer

<400> SEQUENCE: 28
attgcctgag tcagctggga gatgtctttg tcaacttcgt                40

<210> SEQ ID NO 29
<211> LENGTH: 40
<212> TYPE: DNA
<213> ORGANISM: Artificial Sequence
<220> FEATURE:
<223> OTHER INFORMATION: Primer

<400> SEQUENCE: 29
gatttaccgg atgccaggga catggagccg gtgataccgc                40

<210> SEQ ID NO 30
<211> LENGTH: 501
<212> TYPE: DNA
<213> ORGANISM: Artificial Sequence
<220> FEATURE:
<223> OTHER INFORMATION: Synthetically generated oligonucleotide

<400> SEQUENCE: 30
atggccggga caggtatcgc tggcggagta acaggctccc tatctctagc ttccagtaaa     60
agccttctct tcgaggttga caaagatatc tcccacctta cccaggccat agtcaaaaat    120
catcaaaaca tcctccgggt tgcacaatat gcagcccaga atagcgagg attagacctc    180

```
ctattctggg aacaaggggg tttgtgcaaa gccatacagg agcaatgttg cttcctcaat    240
atcagtaaca ctcatgtatc cgtcctccaa gaacggcccc ctcttgaaaa gcgtgtcatc    300
accggttggg gactaaactg ggatcttggt ctgtcccagt gggcacgaga agccctccag    360
acaggcataa ccattctcac cctactcctc cttgtcatat tgtttggccc ctgcatcctc    420
cgccaaatcc aagcccttcc gcagcggtta caaaaccgac atagccagta tgcccttatc    480
aaccaagaga ccatgctata a                                              501
```

<210> SEQ ID NO 31
<211> LENGTH: 40
<212> TYPE: DNA
<213> ORGANISM: Artificial Sequence
<220> FEATURE:
<223> OTHER INFORMATION: Primer

<400> SEQUENCE: 31

```
cgcatatggc cgggacaggt atcgctggcg gagtaacagg                          40
```

<210> SEQ ID NO 32
<211> LENGTH: 40
<212> TYPE: DNA
<213> ORGANISM: Artificial Sequence
<220> FEATURE:
<223> OTHER INFORMATION: Primer

<400> SEQUENCE: 32

```
ctagcttcca gtaaaagcct tctcttcgag gttgacaaag                          40
```

<210> SEQ ID NO 33
<211> LENGTH: 40
<212> TYPE: DNA
<213> ORGANISM: Artificial Sequence
<220> FEATURE:
<223> OTHER INFORMATION: Primer

<400> SEQUENCE: 33

```
ccttacccag gccatagtca aaaatcatca aaacatcctc                          40
```

<210> SEQ ID NO 34
<211> LENGTH: 40
<212> TYPE: DNA
<213> ORGANISM: Artificial Sequence
<220> FEATURE:
<223> OTHER INFORMATION: Primer

<400> SEQUENCE: 34

```
aatatgcagc ccagaataga cgaggattag acctcctatt                          40
```

<210> SEQ ID NO 35
<211> LENGTH: 40
<212> TYPE: DNA
<213> ORGANISM: Artificial Sequence
<220> FEATURE:
<223> OTHER INFORMATION: Primer

<400> SEQUENCE: 35

```
gggggtttgt gcaaagccat acaggagcaa tgttgcttcc                          40
```

<210> SEQ ID NO 36
<211> LENGTH: 40
<212> TYPE: DNA
<213> ORGANISM: Artificial Sequence
<220> FEATURE:
<223> OTHER INFORMATION: Primer

```
<400> SEQUENCE: 36
taacactcat gtatccgtcc tccaagaacg gcccctctt                              40

<210> SEQ ID NO 37
<211> LENGTH: 40
<212> TYPE: DNA
<213> ORGANISM: Artificial Sequence
<220> FEATURE:
<223> OTHER INFORMATION: Primer

<400> SEQUENCE: 37
tcatcaccgg ttggggacta aactgggatc ttggtctgtc                              40

<210> SEQ ID NO 38
<211> LENGTH: 40
<212> TYPE: DNA
<213> ORGANISM: Artificial Sequence
<220> FEATURE:
<223> OTHER INFORMATION: Primer

<400> SEQUENCE: 38
cgagaagccc tccagacagg cataaccatt ctcaccctac                              40

<210> SEQ ID NO 39
<211> LENGTH: 40
<212> TYPE: DNA
<213> ORGANISM: Artificial Sequence
<220> FEATURE:
<223> OTHER INFORMATION: Primer

<400> SEQUENCE: 39
catattgttt ggcccctgca tcctccgcca aatccaagcc                              40

<210> SEQ ID NO 40
<211> LENGTH: 40
<212> TYPE: DNA
<213> ORGANISM: Artificial Sequence
<220> FEATURE:
<223> OTHER INFORMATION: Primer

<400> SEQUENCE: 40
ggttacaaaa ccgacatagc cagtatgccc ttatcaacca                              40

<210> SEQ ID NO 41
<211> LENGTH: 39
<212> TYPE: DNA
<213> ORGANISM: Artificial Sequence
<220> FEATURE:
<223> OTHER INFORMATION: Primer

<400> SEQUENCE: 41
cgctcgagtt atagcatggt ctcttggttg ataagggca                               39

<210> SEQ ID NO 42
<211> LENGTH: 40
<212> TYPE: DNA
<213> ORGANISM: Artificial Sequence
<220> FEATURE:
<223> OTHER INFORMATION: Primer

<400> SEQUENCE: 42
gtcggttttg taaccgctgc ggaagggctt ggatttggcg                              40
```

<210> SEQ ID NO 43
<211> LENGTH: 40
<212> TYPE: DNA
<213> ORGANISM: Artificial Sequence
<220> FEATURE:
<223> OTHER INFORMATION: Primer

<400> SEQUENCE: 43
gggccaaaca atatgacaag gaggagtagg gtgagaatgg                   40

<210> SEQ ID NO 44
<211> LENGTH: 40
<212> TYPE: DNA
<213> ORGANISM: Artificial Sequence
<220> FEATURE:
<223> OTHER INFORMATION: Primer

<400> SEQUENCE: 44
ctggagggct tctcgtgccc actgggacag accaagatcc                   40

<210> SEQ ID NO 45
<211> LENGTH: 40
<212> TYPE: DNA
<213> ORGANISM: Artificial Sequence
<220> FEATURE:
<223> OTHER INFORMATION: Primer

<400> SEQUENCE: 45
cccaaccggt gatgacacgc ttttcaagag ggggccgttc                   40

<210> SEQ ID NO 46
<211> LENGTH: 40
<212> TYPE: DNA
<213> ORGANISM: Artificial Sequence
<220> FEATURE:
<223> OTHER INFORMATION: Primer

<400> SEQUENCE: 46
gatacatgag tgttactgat attgaggaag caacattgct                   40

<210> SEQ ID NO 47
<211> LENGTH: 40
<212> TYPE: DNA
<213> ORGANISM: Artificial Sequence
<220> FEATURE:
<223> OTHER INFORMATION: Primer

<400> SEQUENCE: 47
tttgcacaaa ccccttgtt cccagaatag gaggtctaat                    40

<210> SEQ ID NO 48
<211> LENGTH: 40
<212> TYPE: DNA
<213> ORGANISM: Artificial Sequence
<220> FEATURE:
<223> OTHER INFORMATION: Primer

<400> SEQUENCE: 48
tctgggctgc atattgtgca acccggagga tgttttgatg                   40

<210> SEQ ID NO 49
<211> LENGTH: 40
<212> TYPE: DNA
<213> ORGANISM: Artificial Sequence
<220> FEATURE:
<223> OTHER INFORMATION: Primer

```
<400> SEQUENCE: 49
atggcctggg taaggtggga gatatctttg tcaacctcga                              40

<210> SEQ ID NO 50
<211> LENGTH: 40
<212> TYPE: DNA
<213> ORGANISM: Artificial Sequence
<220> FEATURE:
<223> OTHER INFORMATION: Primer

<400> SEQUENCE: 50
tttactggaa gctagagata gggagcctgt tactccgcca                              40

<210> SEQ ID NO 51
<211> LENGTH: 31
<212> TYPE: DNA
<213> ORGANISM: Artificial Sequence
<220> FEATURE:
<223> OTHER INFORMATION: Primer

<400> SEQUENCE: 51
cgccatgggt gcatccggta atctctgct g                                       31

<210> SEQ ID NO 52
<211> LENGTH: 29
<212> TYPE: DNA
<213> ORGANISM: Artificial Sequence
<220> FEATURE:
<223> OTHER INFORMATION: Primer

<400> SEQUENCE: 52
cgaagcttca ggccccagcc agtcagtac                                         29

<210> SEQ ID NO 53
<211> LENGTH: 29
<212> TYPE: DNA
<213> ORGANISM: Artificial Sequence
<220> FEATURE:
<223> OTHER INFORMATION: Primer

<400> SEQUENCE: 53
cgggatccgc ttccagtaaa agccttctc                                         29

<210> SEQ ID NO 54
<211> LENGTH: 29
<212> TYPE: DNA
<213> ORGANISM: Artificial Sequence
<220> FEATURE:
<223> OTHER INFORMATION: Primer

<400> SEQUENCE: 54
cgaagcttta gtccccaacc ggtgatgac                                         29

<210> SEQ ID NO 55
<211> LENGTH: 267
<212> TYPE: DNA
<213> ORGANISM: Artificial Sequence
<220> FEATURE:
<223> OTHER INFORMATION: Synthetically generated oligonucleotide

<400> SEQUENCE: 55
gcatccggta atctctgct gcacgaagtt gacaaagaca tctcccagct gactcaggca        60
atcgttaaaa accacaaaaa cctgctgaaa atcgcgcagt acgctgcaca gaaccgtcgt      120
ggcctggacc tgctgttctg ggaacagggt ggcctgtgca aagcactgca ggaacagtgc      180
```

```
tgtttcctga acatcactaa ctcccacgtt tctatcctgc aggaacgtcc gccgctggaa    240
aaccgtgtac tgactggctg gggcctg                                       267
```

<210> SEQ ID NO 56
<211> LENGTH: 267
<212> TYPE: DNA
<213> ORGANISM: Artificial Sequence
<220> FEATURE:
<223> OTHER INFORMATION: Synthetically generated oligonucleotide

<400> SEQUENCE: 56

```
gcttccagta aaagccttct cttcgaggtt gacaaagata tctcccacct tacccaggcc     60
atagtcaaaa atcatcaaaa catcctccgg gttgcacaat atgcagccca gaatagacga    120
ggattagacc tcctattctg gaacaagggg ggtttgtgca aagccataca ggagcaatgt    180
tgcttcctca atatcagtaa cactcatgta tccgtcctcc aagaacggcc cctcttgaa     240 aagcgtgtca tcaccggttg gggacta                                       267
```

<210> SEQ ID NO 57
<211> LENGTH: 1008
<212> TYPE: DNA
<213> ORGANISM: Artificial Sequence
<220> FEATURE:
<223> OTHER INFORMATION: Synthetically generated oligonucleotide

<400> SEQUENCE: 57

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatcccc gggaatttcc ggtggtggtg gtggaattct agactccatg    720
ggtgcatccg gtaaatctct gctgcacgaa gttgacaaag acatctccca gctgactcag    780
gcaatcgtta aaaccacaa aaacctgctg aaaatcgcgc agtacgctgc acagaaccgt    840
cgtggcctgg acctgctgtt ctgggaacag ggtggcctgt gcaaagcact gcaggaacag    900 tgctgttttcc tgaacatcac taactcccac gtttctatcc tgcaggaacg tccgccgctg    960
gaaaaccgtg tactgactgg ctggggcctg aagcttaatt catcgtga                008
```

<210> SEQ ID NO 58
<211> LENGTH: 963
<212> TYPE: DNA
<213> ORGANISM: Artificial Sequence
<220> FEATURE:
<223> OTHER INFORMATION: Synthetically generated oligonucleotide

```
<400> SEQUENCE: 58 atgtcccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgtttaaa    540
aaacgtattg aagctatccc acaaattgat aagtacttga atccagcaa gtatatagca    600
tggcctttgc agggctggca agccacgttt ggtggtggcg accatcctcc aaaatcggat   660
ctggttccgc gtggatccgc ttccagtaaa gccttctct tcgaggttga caaagatatc    720
tcccaccta cccaggccat agtcaaaaat catcaaaaca cctccgggt tgcacaatat     780
gcagcccaga atagacgagg attagacctc ctattctggg aacaagggg tttgtgcaaa    840
gccatacagg agcaatgttg cttcctcaat atcagtaaca ctcatgtatc cgtcctccaa   900
gaacggcccc ctcttgaaaa gcgtgtcatc accggttggg gactaaagct taattcatcg   960
tga                                                                963

<210> SEQ ID NO 59
<211> LENGTH: 759
<212> TYPE: DNA
<213> ORGANISM: Artificial Sequence
<220> FEATURE:
<223> OTHER INFORMATION: Synthetically generated oligonucleotide

<400> SEQUENCE: 59
atgtctgata aaattattca tctgactgat gattcttttg atactgatgt acttaaggca    60
gatggtgcaa tcctggttga tttctgggca cactggtgcg gtccgtgcaa aatgatcgct   120
ccgattctgg atgaaatcgc tgacgaatat caggggcaaac tgaccgttgc aaaactgaac   180
atcgatcaca acccgggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggc tctggatccg gtgatgacga tgacaaggta   360
cccatgggca gcagccatca tcatcatcat cacagcagcg gcctggtgcc gcgcggcagc   420
catatggcat ccggtaaatc tctgctgcac gaagttgaca aagacatctc ccagctgact   480
caggcaatcg ttaaaaacca caaaaacctg ctgaaaatcg cgcagtacgc tgcacagaac   540
cgtcgtggcc tggacctgct gttctgggaa cagggtggcc tgtgcaaagc actgcaggaa   600
cagtgctgtt tcctgaacat cactaactcc cacgtttcta tcctgcagga acgtccgccg   660
ctggaaaacc gtgtactgac tggctggggc ctgctcgaga tcttcgaatt ccgcggccgc   720
aggcctctag agtcgacctg cagtaatcgt acagggtag                           759

<210> SEQ ID NO 60
<211> LENGTH: 759
<212> TYPE: DNA
<213> ORGANISM: Artificial Sequence
<220> FEATURE:
<223> OTHER INFORMATION: Synthetically generated oligonucleotide
```

-continued

```
<400> SEQUENCE: 60
atgtctgata aaattattca tctgactgat gattcttttg atactgatgt acttaaggca      60
gatggtgcaa tcctggttga tttctgggca cactggtgcg gtccgtgcaa aatgatcgct     120
ccgattctgg atgaaatcgc tgacgaatat cagggcaaac tgaccgttgc aaaactgaac     180
atcgatcaca acccgggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggc tctggatccg gtgatgacga tgacaaggta     360
cccatgggca gcagccatca tcatcatcat cacagcagcg gcctggtgcc gcgcggcagc     420
catatggctt ccagtaaaag ccttctcttc gaggttgaca aagatatctc ccaccttacc     480
caggccatag tcaaaaatca tcaaaacatc ctccggttg cacaatatgc agcccagaat     540
agacgaggat tagacctcct attctgggaa caaggggtt tgtgcaaagc catacaggag     600
caatgttgct tcctcaatat cagtaacact catgtatccg tcctccaaga acggccccct     660
cttgaaaagc gtgtcatcac cggttgggga ctactcgaga tcttcgaatt ccgcggccgc     720
aggcctctag agtcgacctg cagtaatcgt acagggtag                           759
```

ANTIGENIC FRAGMENT OF HUMAN T-LYMPHOTROPIC VIRUS

BACKGROUND OF THE INVENTION

1. Field of the Invention

The present invention relates to human T-lymphotropic virus (HTLV). More particularly, the present invention relates to antigenic fragments of HTLV.

2. Description of the Related Arts

Human T-lymphotropic virus (HTLV) classified into Retroviridae was the first human retrovirus to be isolated. HTLV type I was first isolated in 1978 whereas HTLV type II was in 1982. HTLV is spread by sexual contact, from mother to child and through contaminated blood product. It is endemic in southern Japan, Caribbean, South Africa and Melanesia. To avoid viral transmission, screening of blood donations for HTLV is now routinely carried out in many countries. Since 1996, antibodies of HTLV-I and HTLV-II have been screening by ELISA and western blotting in Taiwan.

The preliminary screening of HTLV is carried out by ELISA, and a final diagnosis can be made by western blotting and polymerase chain reaction. The commercialized HTLV assay utilizes viral total lysate as antigen to detect specific antibodies from carrier blood. For higher sensitivity and specificity, a peptide fragment of viral envelop can be used as an additional antigen. The preparation of viral total lysate is complicated and has a potential risk; there is, therefore, still a need for a safe and effective HTLV antigen.

SUMMARY OF THE INVENTION

It is therefore a primary object of the present invention to provide fusion proteins of human T-lymphotropic virus (HTLV) with Glutathione S-transferase (GST) or Thioredoxin. The fusion proteins have the advantage of high specific and sensitive to HTLV-I/II and the preparation of these proteins is safe and effective. In addition, the fusion proteins can be applied in HTLV-I/II assay. Using genomic engineering, the antigenic viral recombinant protein expressed by E. coli can be prepared in large quantities at low cost. Moreover, avoiding the cultivation and purification of HTLV, the preparation of the present invention is safer than the current preparation.

Accordingly, in a first aspect, the invention features an isolated peptide comprising an antigenic fragment of HTLV-I gp21 having the amino acid sequence of SEQ ID No: 3.

The invention also features an isolated peptide comprising an antigenic fragment of HTLV-II gp21 having the amino acid sequence of SEQ ID No: 4.

In addition, the present invention features an isolated nucleic acid encoding an antigenic fragment of HTLV-I gp21, wherein the nucleic acid comprises the nucleotide sequence of SEQ ID No: 55.

The present invention also features an isolated nucleic acid encoding an antigenic fragment of HTLV-II gp21, wherein the nucleic acid comprises the nucleotide sequence of SEQ ID No: 56.

Both of the aforementioned nucleic acids encoding antigenic fragments in the invention can be optionally combined with glutathione S-transferase (GST) or thioredoxin (thio) to form 4 recombinant nucleic acids as below.

1. A nucleic acid encoding GST/HTLV-I gp21 fusion protein, wherein the nucleic acid comprises the nucleotide sequence of SEQ ID No: 57.

2. A nucleic acid encoding Thio/HTLV-I gp21 fusion protein, wherein the nucleic acid comprises the nucleotide sequence of SEQ ID No: 59.

3. A nucleic acid encoding GST/HTLV-II gp21 fusion protein, wherein the nucleic acid comprises the nucleotide sequence of SEQ ID No: 58.

4. A nucleic acid encoding Thio/HTLV-II gp21 fusion protein, wherein the nucleic acid comprises the nucleotide sequence of SEQ ID No: 60.

In addition, the present invention also features an expression vector comprising a nucleic acid encoding any of the four fusion proteins operably linked to a nucleotide sequence regulatory element that controls expression of the nuleic acid and a process for producing the HTLV antigenic fragments. The process comprises introducing an expression vector comprising a nucleic acid encoding any of the four fusion proteins into a cell, culturing the cell under conditions suitable for production of the fusion protein, and recovering the fusion protein from the cell culture.

In one embodiment of the process, the cell is *Escherichia coli*, for example, BL21(DE3) strain. For the production of GST/HTLV gp21 fusion protein, recovery is enabled by glutathione sepharose column; for the production of Thio/HTLV gp21 fusion protein, recovery is enabled by Ni-NTA column.

Accordingly, the four nucleic acids encode four fusion proteins as below.

1. GST/HTLV-I gp21 fusion protein comprising the amino acid sequence of SEQ ID No: 5.

2. Thio/HTLV-I gp21 fusion protein comprising the amino acid sequence of SEQ ID No: 7.

3. GST/HTLV-II gp21 fusion protein comprising the amino acid sequence of SEQ ID No: 6.

4. Thio/HTLV-II gp21 fusion protein comprising the amino acid sequence of SEQ ID No: 8.

Another aspect of the invention features a kit for the detection of human T-lymphotrophic virus (HTLV). The kit comprises a solid substrate, a first HTLV gp21 antigenic fragment immobilized on the solid substrate, a blocking solution for blocking a HTLV gp21 antigenic fragment-unbound region on the solid substrate, a second HTLV gp21 antigenic fragment, a wash solution, and a signal-producing means operably linked to the second HTLV gp21 antigenic fragment to produce a signal, wherein the first and second HTLV gp21 are selected from any of the fusion proteins.

In one embodiment of the kit in the invention, the first HTLV gp21 is Thio/HTLV-II gp21 fusion protein, and the second HTLV gp21 is GST/HTLV-I gp21 fusion protein.

BRIEF DESCRIPTION OF THE DRAWINGS

The present invention will be more fully understood and further advantages will become apparent when reference is made to the following description of the invention and the accompanying drawings in which:

FIGS. 1A and 1B show nucleotide sequences of HTLV antigenic fragment. FIG. 1A represents the entire sequence of HTLV-I gp21 (SEQ ID No:9); and FIG. 1B represents the entire sequence of HTLV-II gp21 (SEQ ID No:30).

FIGS. 3A–3C shows vector pThioHis B (3A), and the construct pThio/HTLV-I gp21 (3B) as well as the construct pThio/HTLV-II gp21 (3C).

DETAILED DESCRIPTION OF THE INVENTION

Figure 2A:
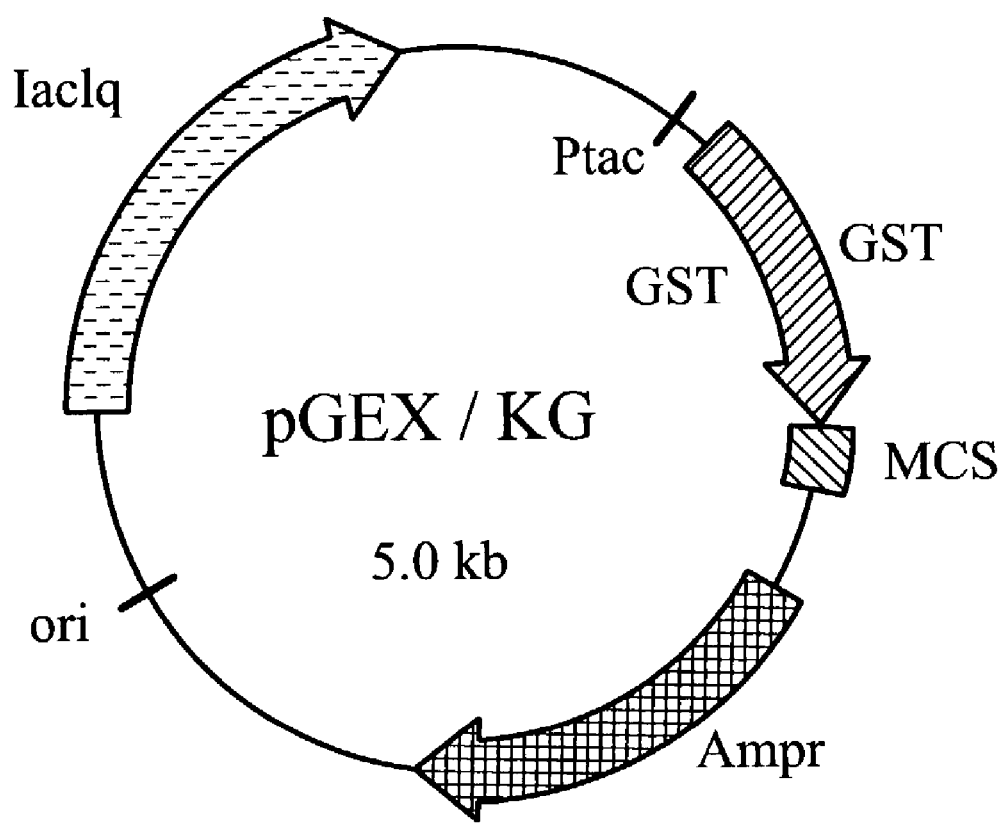
FIGS. 2A–2C shows vector pGEX-KG (2A), and the construct pGST/HTVL-I gp21 (2B) as well as the construct pGST/HTLV-II gp21 (2C).

HTLV is classified as HTLV-I and HTLV-II; diseases caused by HTLV-I include adult T-cell leukemia/lymphoma (ATL) developed by about 2–3% of infected patients, HTLV-I-associated myelopathy/tropical spastic paraparesis (HAM/TSP) developed by only 2–3% of infected patients, generally appearing in middle age (40~50 yrs). For those infected by transfusion, however, the duration shortens to one month to 4 years, with 95% of infected patients experiencing no lifelong symptoms. HTLV-II is considered to act as associated with a typical hairy cell leukemia.

HTLV genome is ss(+)RNA composed of gag, pol, env, tax and rex genes. gag gene is translated into a polyprotein, and then spliced into mature core proteins: p19, p24, p15, etc. pol gene is translated into reverse transcriptase, integrase, and RNAse H. env gene is translated into envelop proteins p21 and p46. tax and rex genes are associated with viral replication. After infection, HTLV induces human antibodies against viral gag protein, mainly p24. The antibody arises 2 months after infection and then antibodies against viral surface protein are produced.

The present invention is based on the discovery of a region rich in antigenic determinants in HTLV-I gp21 (SEQ ID No: 1) and HTLV-II gp21 (SEQ ID No:2) by antigenic determinant analysis of HTLV-I/II. The region is shown below.

antigenic fragment of HTLV-I gp21, wherein the nucleic acid comprises the nucleotide sequence of SEQ ID No: 55, and an isolated nucleic acid encoding an antigenic fragment of HTLV-II gp21, wherein the nucleic acid comprises the nucleotide sequence of SEQ ID No: 56.

Any of the aforementioned antigenic fragments can be optionally combined with glutathione S-transferase (GST) or thioredoxin (thio) to form 4 recombinant nucleic acids as below.

1. A nucleic acid encoding GST/HTLV-I gp21 fusion protein, wherein the nucleic acid comprises the nucleotide sequence of SEQ ID No: 57.

2. A nucleic acid encoding Thio/HTLV-1 gp21 fusion protein, wherein the nucleic acid comprises the nucleotide sequence of SEQ ID No: 59.

3. A nucleic acid encoding GST/HTLV-II gp21 fusion protein, wherein the nucleic acid comprises the nucleotide sequence of SEQ ID No: 58.

4. A nucleic acid encoding Thio/HTLV-II gp21 fusion protein, wherein the nucleic acid comprises the nucleotide sequence of SEQ ID No: 60.

In addition, the scope of the invention also includes an expression vector comprising a nucleic acid encoding any of the four fusion proteins operably linked to a nucleotide sequence regulatory element that controls expression of the nucleic acid, and a process for producing the HTLV antigenic fragments. The process comprises introducing a expression vector comprising a nucleic acid encoding any of the four fusion proteins into a cell, culturing the cell under conditions suitable for production of the fusion protein, and recovering the fusion protein from the cell culture.

```
HTLV-I gp21 fragment (SEQ ID No: 3)

A  S  G  K  S  L  L |H  E  V  D  K  D  I  S  Q  L| T  Q  A  I  V  K  N  H  K  N  L  L  K

I  A  Q  Y  A |A  Q  N  R  R  G  L  D  L  L| F  W  E  Q  G  G  L  C  K  A  L  Q  E  Q  C

C  F  L  N  I  T  N  S  H  V  S |I  L  Q  E  R  P  P  L  E  N| R  V  L  T  G  W  G  L

HTLV-II gp21 fragment (SEQ ID No: 4)

A  S  S  K  S  L  L |F  E  V  D  K  D  I  S  H  L| T  Q  A  I  V  K  N  H  Q  N  I  L  R

V  A  Q  Y  A |A  Q  N  R  R  G  L  D  L  L| F  W  E  Q  G  G  L  C  K  A  I  Q  E  Q  C

C  F  L  N  I  S  N  T  H  V  S |V  L  Q  E  R  P  P  L  E  K| R  V  I  T  G  W  G  L
```

The frame regions indicate antigenic determinants.

Using assembly PCR, modified HTLV-I gp21 and HTLV-II gp21 genes were synthesized according to the gene sequence from genebank. The HTLV-I gp21 gene was modified with *E. coli* preferred codons. Using these sequences as templates, gp21 fragments with 270 bp were amplified by PCR and cloned into pGEX-KG or pThioHisB.

Therefore, the present invention features two isolated peptides, an isolated peptide comprising an antigenic fragment of HTLV-I gp21 having the amino acid sequence of SEQ ID No: 3, and an isolated peptide comprising an antigenic fragment of HTLV-II gp21 having the amino acid sequence of SEQ ID No: 4.

The two peptides of the present invention are encoded from two nucleic acids, an isolated nucleic acid encoding an Examples of the expression vector include pGST/HTLV-I gp21, pThio/HTLV-I gp21, pGST/HTLV-II gp21, and pThio/HTLV-II gp21. The aforementioned expression vectors have been deposited in the Bioresources collection and research center in Taiwan, Republic of China, and the depository numbers are 940407, 940405, 940408, and 940406, respectively. They have also been deposited in the American Type Culture Collection, 1801 University Blvd. Manassas. Va. on May 30, 2003, and the depository numbers are PTA-5238, PTA-5240, PTA-5239, and PTA-5241, respectively.

In one embodiment of the process, the cell is *Escherichia coli*, for example, BL21(DE3) strain. For the production of GST/HTLV gp21 fusion protein, recovery is enabled by glutathione sepharose column; for the production of Thio/HTLV gp21 fusion protein, recovery is enabled by Ni-NTA affinity column.

Accordingly, the four nucleic acids encode four fusion proteins as below.

1. GST/HTLV-I gp21 fusion protein comprising the amino acid sequence of SEQ ID No: 5.
2. Thio/HTLV-I gp21 fusion protein comprising the amino acid sequence of SEQ ID No: 7.
3. GST/HTLV-II gp21 fusion protein comprising the amino acid sequence of SEQ ID No: 6.
4. Thio/HTLV-II gp21 fusion protein comprising the amino acid sequence of SEQ ID No: 8.

The invention also features a kit for the detection of human T-lymphotrophic virus (HTLV). The kit comprises a solid substrate, a first HTLV gp21 antigenic fragment immobilized on the solid substrate, a blocking solution for blocking a HTLV gp21 antigenic fragment-unbound region on the solid substrate, a second HTLV gp21 antigenic fragment, a wash solution, and a signal-producing means operably linked to the second HTLV gp21 antigenic fragment to produce a signal, wherein the first and second HTLV gp21 are selected from any of the fusion proteins.

In one embodiment of the kit in the invention, the first HTLV gp21 is Thio/HTLV-II gp21 fusion protein, and the second HTLV gp21 is GST/HTLV-I gp21 fusion protein.

The solid substrate of the kit includes, but is not limited to, glass, silicon, ceramic, metal, or organic polymer such as styrene, ethylene, propylene, ester, acrylic acid, acrylic ester, alkyl acrylic acid, or alkyl acrylic ester.

The blocking solution includes a solution of BSA, casein, or gelatin.

The wash solution includes PBS, TBS, or PBST with 0.05% Tween 20.

The signal producing means includes radioactive label, fluorescent label, phosphorescent label, luminescent label, or enzyme. The luminescent label includes biological luminescent label or chemical luminescent label. The enzyme includes alkaline phosphatase, hydrogen peroxidase, or β-galactosidase. In one embodiment, the kit further comprises a substrate, and the susbtrate reacts with the enzyme to produce a color.

In another embodiment of the detection kit of HTLV, the signal producing means further includes a biotin and a avidin, the avidin operably binding to the radioactive label, fluorescent label, phosphorescent label, luminescent label, or enzyme. The enzyme includes alkaline phosphatase, hydrogen peroxidase, or β-galactosidase. In addition, the kit further comprises a substrate, and the susbtrate reacts with the enzyme to produce a color.

EXAMPLE 1

Assembly PCR for the Synthesis of HTLV-I/II gp21

HTLV-I gp21 gene sequence from GeneBank D13784 was modified with *E. coli* preferred codons. 20 primers were designed for assembly PCR to synthesize HTLV-I gp21 of 505 bp as shown in FIG. 1A (SEQ ID No: 9). The two ends were designed with Nde I (5') and Xho I (3') restriction sites. The 20 primers are shown below.

```
I F1:   CGCAT ATGGG TGCAG GCGTT GCTGG CGGTA TCACC GGCTC         (SEQ ID No:10)

I F2:   TGGCA TCCGG TAAAT CTCTG CTGCA CGAAG TTGAC AAAGA         (SEQ ID No:11)

I F3:   AGCTG ACTCA GGCAA TCGTT AAAAA CCACA AAAA CCTGC T        (SEQ ID No:12)

I F4:   CGCAG TACGC TGCAC AGAAC CGTCG TGGCC TGGAC CTGCT         (SEQ ID No:13)

I F5:   AACAG GGTGG CCTGT GCAAA GCACT GCAGG AACAG TGCTG         (SEQ ID No:14)

I F6:   ACATC ACTAA CTCCC ACGTT TCTAT CCTGC AGGAA CGTCC         (SEQ ID No:15)

I F7:   AAAAC CGTGT ACTGA CTGGC TGGGG CCTGA ACTGG GACCT         (SEQ ID No:16)

I F8:   CTCAG TGGGC TCGTG AGGCG CTGCA GACTG GTATC ACCCT         (SEQ ID No:17)

I F9:   TGCTG CTGCT GGTTA TCCTG GCAGG TCCGT GCATC CTGCG         (SEQ ID No:18)

I F10:  GTCAC CTGCC GTCTC GTGTA CGTTA CCCGC ACTAC TCTCT         (SEQ ID No:19)

I R1:   CGCTC GAGTT ACAGG GAAGA TTCCG GTTTG ATCAG AGAGT AGTGC GGGT  (SEQ ID No:20)

I R2:   CGAGA CGGCA GGTGA CGCAG CTGAC GCAGG ATGCA CGGAC         (SEQ ID No:21)

I R3:   ATAAC CAGCA GCAGC AGCGC AACCA GGGTG ATACC AGTCT         (SEQ ID No:22)

I R4:   TCACG AGCCC ACTGA GACAG GCCCA GGTCC CAGTT CAGGC         (SEQ ID No:23)

I R5:   GTCAG TACAC GGTTT TCCAG CGGCG GACGTT CCTGC AGGA         (SEQ ID No:24)

I R6:   TGGGA GTTAG TGATG TTCAG GAAAC AGCAC TGTTC CTGCA         (SEQ ID No:25)

I R7:   CACAG GCCAC CCTGT TCCCA GAACA GCAGG TCCAG GCCAC         (SEQ ID No:26)

I R8:   TGTGC AGCGT ACTGC GCGAT TTTCA GCAGG TTTTT GTGGT         (SEQ ID No:27)

I R9:   ATTGC CTGAG TCAGC TGGGA GATGT CTTTG TCAAC TTCGT         (SEQ ID No:28)

I R10:  GATTT ACCGG ATGCC AGGGA CATGG AGCCG GTGAT ACCGC         (SEQ ID No:29)
```

According to HTLV-II gp21 gene sequence from GeneBank NC_001488, 20 primers were designed for assembly PCR to synthesize HTLV-II gp21 of 514 bp as shown in FIG. 1B (SEQ ID No: 30). The two ends were designed with Nde I (5') and Xho I (3') restriction sites. The 20 primers are shown below.

```
II F1:   CGCAT ATGGC CGGGA CAGGT ATCGC TGGCG GAGTA ACAGG     (SEQ ID No:31)

II F2:   CTAGC TTCCA GTAAA AGCCT TCTCT TCGAG GTTGA CAAAG     (SEQ ID No:32)

II F3:   CCTTA CCCAG GCCAT AGTCA AAAAT CATCA AACA  TCCTC     (SEQ ID No:33)

II F4:   AATAT GCAGC CCAGA ATAGA CGAGG ATTAG ACCTC CTATT     (SEQ ID No:34)

II F5:   GGGGG TTTGT GCAAA GCCAT ACAGG AGCAA TGTTG CTTCC     (SEQ ID No:35)

II F6:   TAACA CTCAT GTATC CGTCC TCCAA GAACG GCCCC CTCTT     (SEQ ID No:36)

II F7:   TCATC ACCGG TTGGG GACTA AACTG GGATC TTGGT CTGTC     (SEQ ID No:37)

II F8:   CGAG AAGCC CTCCA GACAG GCATA ACCAT TCTCA CCCTA C     (SEQ ID No:38)

II F9:   CATAT TGTTT GGCCC CTGCA TCCTC CGCCA AATCC AAGCC     (SEQ ID No:39)

II F10:  GGTTA CAAAA CCGAC ATAGC CAGTA TGCCC TTATC AACCA     (SEQ ID No:40)

II R1:   CGCTC GAGTT ATAGC ATGGT CTCTT GGTTG ATAAG GGCA      (SEQ ID No:41)

II R2:   GTCGG TTTTG TAACC GCTGC GGAAG GGCTT GGATT TGGCG     (SEQ ID No:42)

II R3:   GGGCC AAACA ATATG ACAAG GAGGA GTAGG GTGAG AATGG     (SEQ ID No:43)

II R4:   CTGGA GGGCT TCTCG TGCCC ACTGG GACAG ACCAA GATCC     (SEQ ID No:44)

II R5:   CCCAA CCGGT GATGA CACGC TTTTC AAGAG GGGGC CGTTC     (SEQ ID No:45)

II R6:   GATAC ATGAG TGTTA CTGAT ATTGA GGAAG CAACA TTGCT     (SEQ ID No:46)

II R7:   TTTGC ACAAA CCCCC TTGTT CCCAG AATAG GAGGT CTAAT     (SEQ ID No:47)

II R8:   TCTGG GCTGC ATATT GTGCA ACCCG GAGGA TGTTT TGATG     (SEQ ID No:48)

II R9:   ATGGC CTGGG TAAGG TGGGA GATAT CTTTG TCAAC CTCGA     (SEQ ID No:49)

II R10:  TTTAC TGGAA GCTAG AGATA GGGAG CCTGT TACTC CGCCA     (SEQ ID No:50)
```

EXAMPLE 2

Construction of pHTLV gp21

The fragments amplified by assembly PCR were separated by 2% agarose gel and purified by QIAquick Gel Extraction Kit (QIAGEN). DNA was eluted with 50 µl elution buffer (10 mM Tris-Cl, pH 8.5), and treated by Nde I and Xho I. pET15b was also treated by Nde I and Xho I, separated by 0.8% agarose gel, and purified by QIAquick Gel Extraction Kit (QIAGEN) to obtain a DNA fragment of 2900 bp. Ligation of the pET15b and HTLV gp21 fragment was performed by DNA Ligation Kit (TaKaRa) at 16° C. for 40 min. The ligation product was transformed into DH5a competent cell. The recombinant constructs were analyzed and designated "pB119/HTLV-I gp21" and "pB119/HTLV-II gp21" respectively.

EXAMPLE 3

Construction of pGST/HTLV-I/II gp21

Using pB119/HTLV-I gp21 or pB119/HTLV-II gp21 as template, HTLV gp21 antigenic fragment of 270 bp was amplified with two sets of primers: two ends of HTLV-I gp21 fragments were designed with NcoI (5') and Hind III (3') restriction sites, and two ends of HTLV-II gp21 fragments were designed with BamHI (5') and Hind III (3') restriction sites.

```
I  gp21 (270)/GST F:  CGCCA TGGGT GCATC CGGTA AATCT CTGCT G     (SEQ ID No:51)

I  gp21 (270)/GST R:  CGAAG CTTCA GGCCC CAGCC AGTCA GTAC        (SEQ ID No:52)

II gp21 (270)/GST F:  CGGGA TCCGCTTC CAGTA AAAGC CTTCT C         (SEQ ID No:53)

II gp21 (270)/GST R:  CGAAG CTTTA GTCCC CAACC GGTGA TGAC        (SEQ ID No:54)
```

Figure 2B:
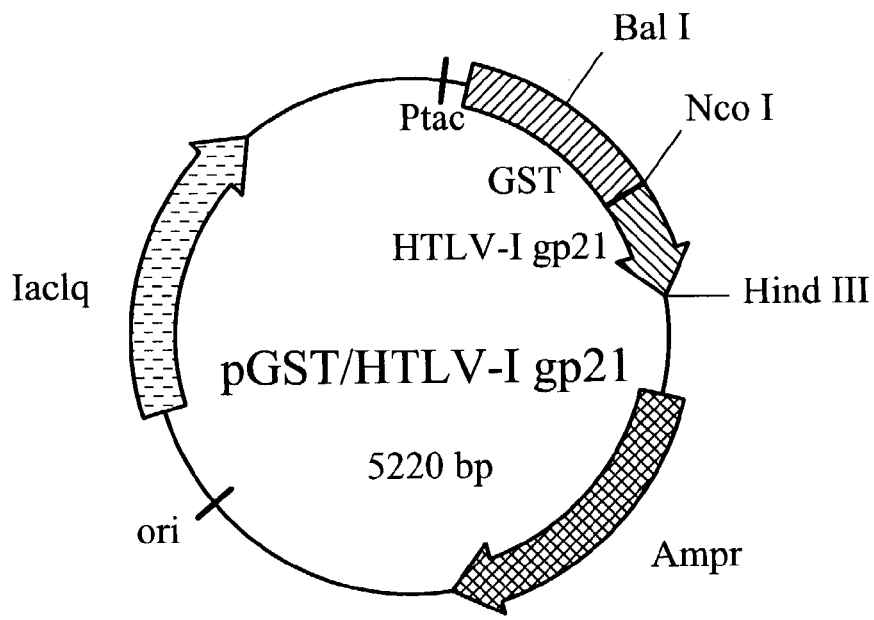
Figure 2C:
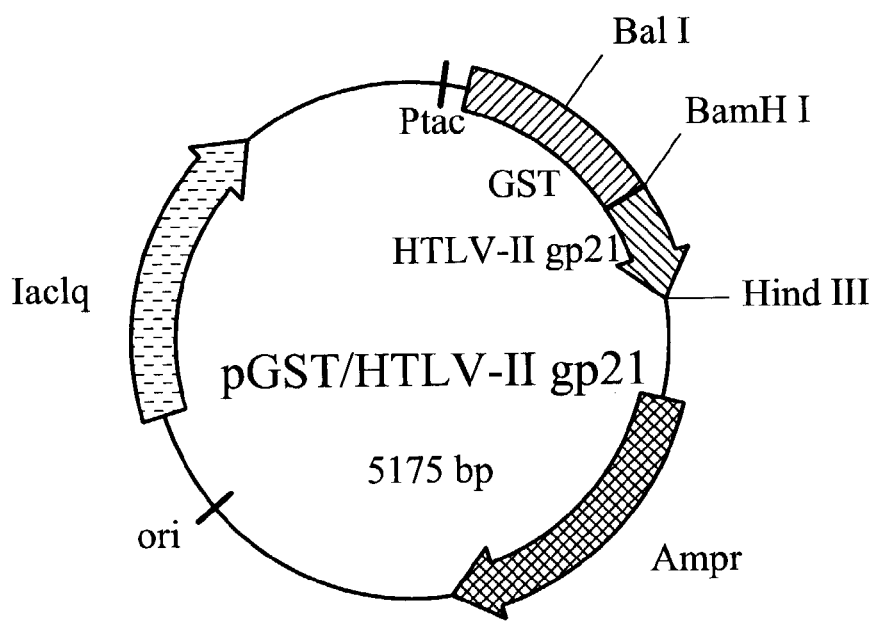

The fragments obtained are as shown in SEQ ID No: 55 and 56. The two fragments were cloned into PGEX-KG as in the map shown in FIG. 2A and designated pGST/HTLV-I gp21 and pGST/HTLV-II gp21, as shown in FIGS. 2B and 2C, respectively. The nucleotide sequence of GST/HTLV-I gp21 is shown as SEQ ID No: 57, whereas that of GST/HTLV-II gp21 is shown as SEQ ID No: 58.

EXAMPLE 4

Figure 3A:
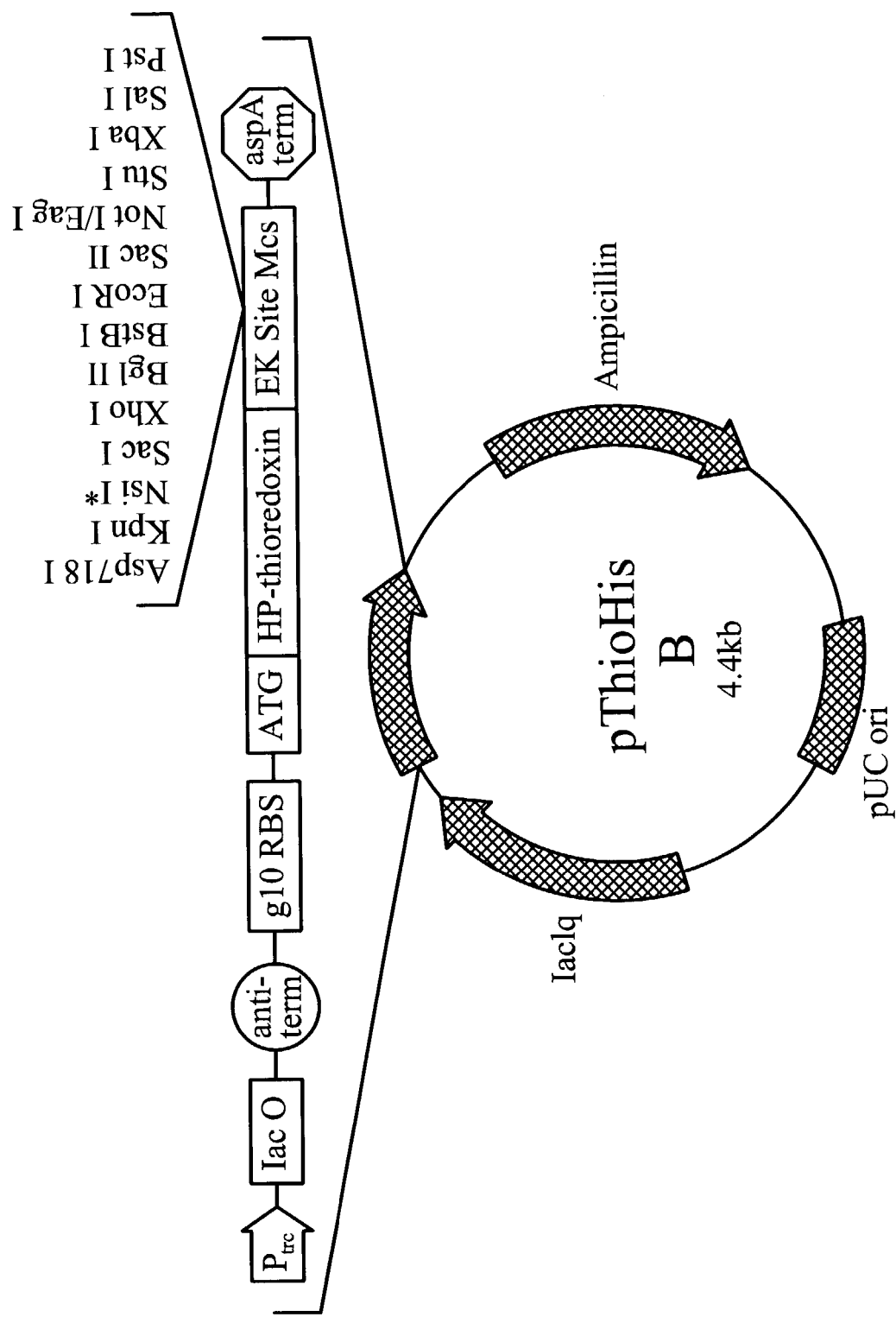
Figures 3B, 3C:
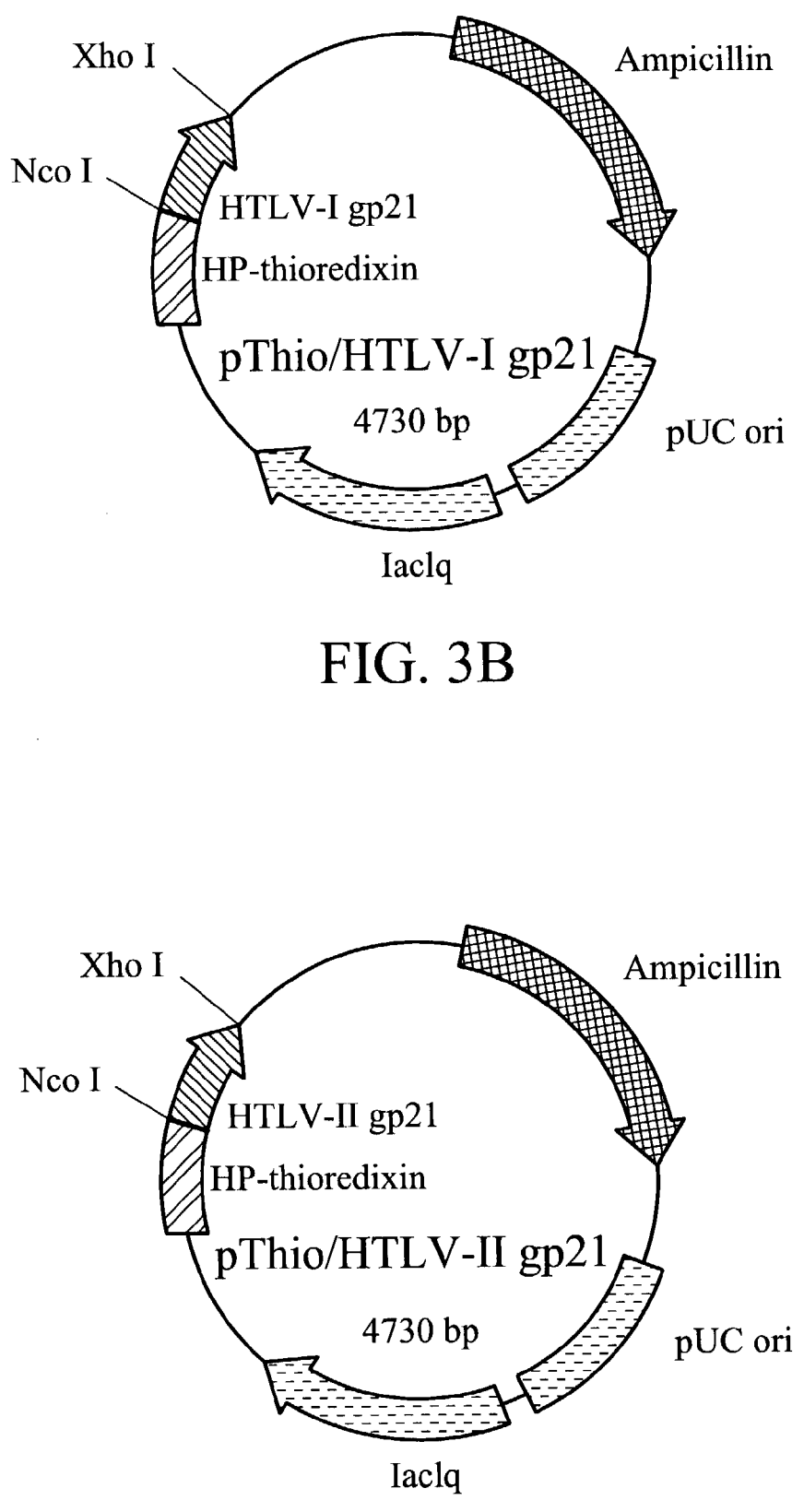

Construction of pThioredoxin/HTLV-I/II gp21 pB119/HTLV-I gp21 or pB119/HTLV-II gp21 were treated with NcoI (5') and Xho I (3') to obtain gp 21 fragments with 6 histidine on the N end. The gp21 fragments were subcloned into pThioHisB (Invitrogen) as the map shown in FIG. 3A. The resulting expression constructs were designated pThio/HTLV-I gp21 and pThio/HTLV-II gp21 as shown in FIGS. 3B and 3C respectively. The nucleotide sequence of Thio/HTLV-I gp21 is shown as SEQ ID No: 59, whereas that of Thio/HTLV-II gp21 is as SEQ ID No: 60.

EXAMPLE 5

IPTG Induction of Protein Expression

The expression constructs were transformed into BL21 (DE3) expression host and 200 rpm vibration-cultured in 1 L of LB/Amp at 37° C. Bacteria were grown to $O.D._{595}=0.8$, and 1 mL of the bacteria culture was sidelined for "expression control" (T0). 1 mL of 1M IPTG (isopropyl-b-D-thiogalactopyranoside) was added to the rest of the culture to induce protein expression. After 3 hr induction, 1 mL of the bacteria culture was sidelined as Ta. The bacteria harvested at different time intervals were lysed with lysis buffer separately. The volume of the lysis buffer varies according to the equation of O.D.xvolume (μl)/20=lysis buffer volume (μl). An equal volume of sample buffer was then added and the reaction was heated at 95° C. for 5 min. 10 μl of the sample was analyzed by SDS-PAGE. The rest of the culture was centrifuged at 8000 rpm for 15 min to collect bacteria for subsequent preotein purification.

EXAMPLE 6

Confirmation of the Expressed Protein Forms

The centrifuged bacteria were resuspended and homogenized with 100 mL IMAC-5 with 0.1% Triton-100. The bacteria were lyzed by microfluidizer and centrifuged at 15000 rpm for 30 min to separate supernatant and pellet. The expressed protein was confirmed with SDS-PAGE for soluble form and inclusion body.

EXAMPLE 7

Purification of GST Fusion Protein

GST/HTLV-I gp21 (33 kDa) or GST/HTLV-II gp21 (33 kDa) were purified by Glutathione Sepharose™ 4B (Amersham Pharmacia Biotech). The centrifuged bacteria were resuspended and homogenized with 100 mL IMAC-5 with 0.1% Triton-100. The bacteria were lyzed by microfluidizer and centrifuged at 15000 rpm for 30 min to separate supernatant. 2 mL Glutathione Sepharose™ 4B column was prepared and balanced with 10 mL IMAC-5 with 0.1% Triton-100. 50 mL supernatant was passed through the column twice. Unbound protein and impurities were washed out by 10 mL IMAC-5 with 0.1% Triton-100. Finally, GST fusion protein was eluted with 30 mL of 10 mM Glutathione.

EXAMPLE 8

Purification of Thioredoxin Fusion Protein by Ni-NTA Affinity Column

For the purification of Thio/HTLV-I gp21 and Thio/HTLV-II gp21 in the form of inclusion bodies, the unsoluble pellets after homogenization were resuspended with 60 mL IMAC-5 with 8M Urea and stirred overnight. The solution was centrifuged at 15000 rpm for 30 min to obtain the supernatant. The supernatant was passed through 2.5 mL Ni-NTA affinity column twice or 3 times. The impurities were washed away with the buffer listed below in sequence: Buffer B (8M urea, 0.1M $NaH_2PO_4$, 0.001M Tris.HCl, pH 8.0); Buffer C (8M urea, 0.1M $NaH_2PO_4$, 0.001M Tris.HCl, pH 6.3); Buffer D (8M urea, 0.1M $NaH_2PO_4$, 0.001M Tris.HCl, pH 5.9); Buffer E (8M urea, 0.1M $NaH_2PO_4$, 0.001M Tris.HCl, pH 4.5). The final protein was eluted with 8M urea containing 100 mM EDTA. All steps were performed at room temperature.

EXAMPLE 9

Analysis of HTLV-I/II Antigenic Protein

Figure 4:
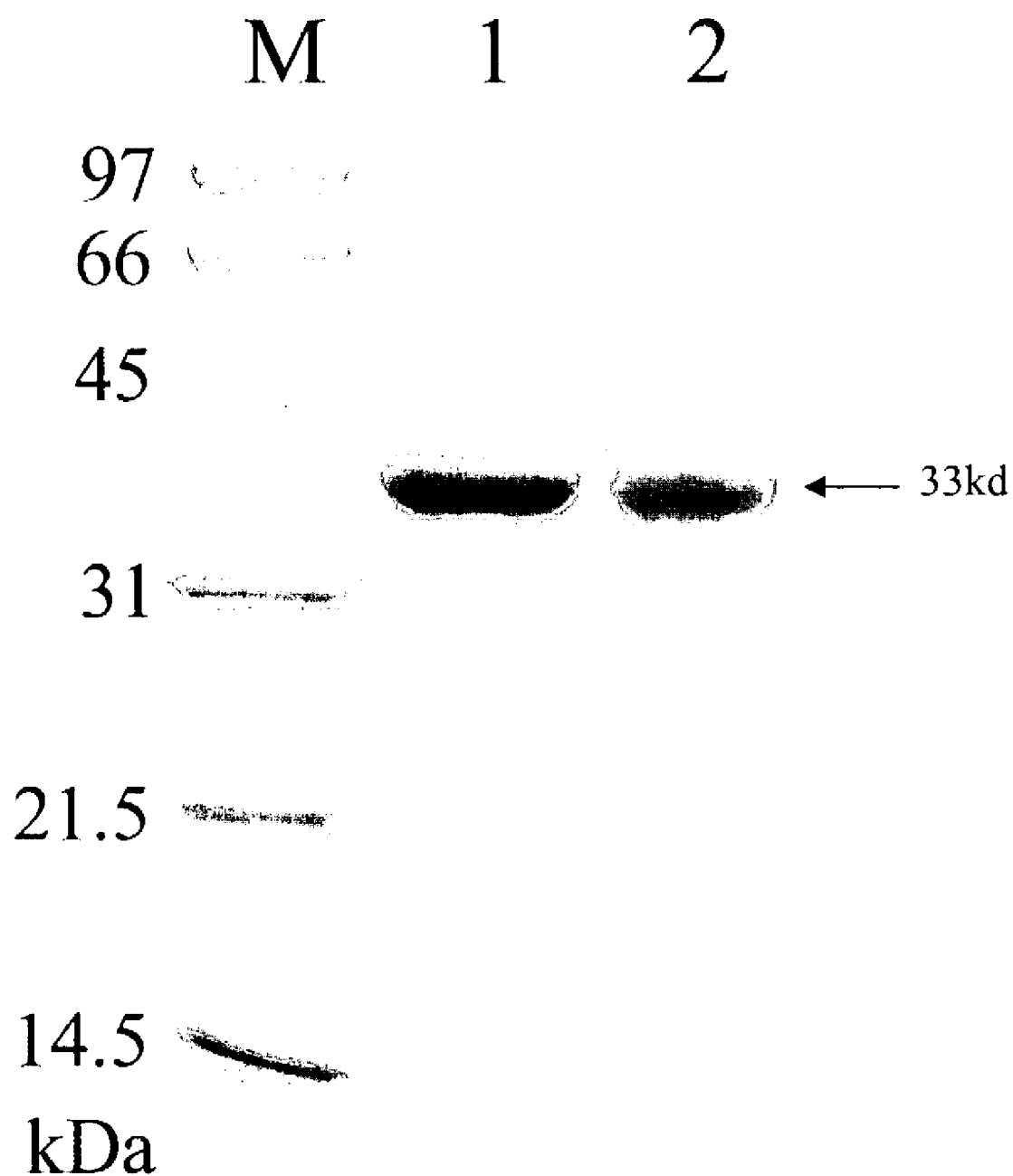
FIG. 4 represents a SDS-PAGE analysis for purified GST/HTLV-I gp21 (lane 1) and GST/HTLV-II gp21 (lane 2) fusion proteins (33 kDa).

The fusion protein GST/HTLV-I/II gp21 was prepared to increase protein expression and soluble form protein. The results of purified fusion protein GST/HTLV-I/II gp21 are shown in FIG. 4, GST/HTLV-I gp21 (lane 1) and GST/HTLV-II gp21 (lane 2) are both 33 kDa and purity over 90%.

Figure 5:
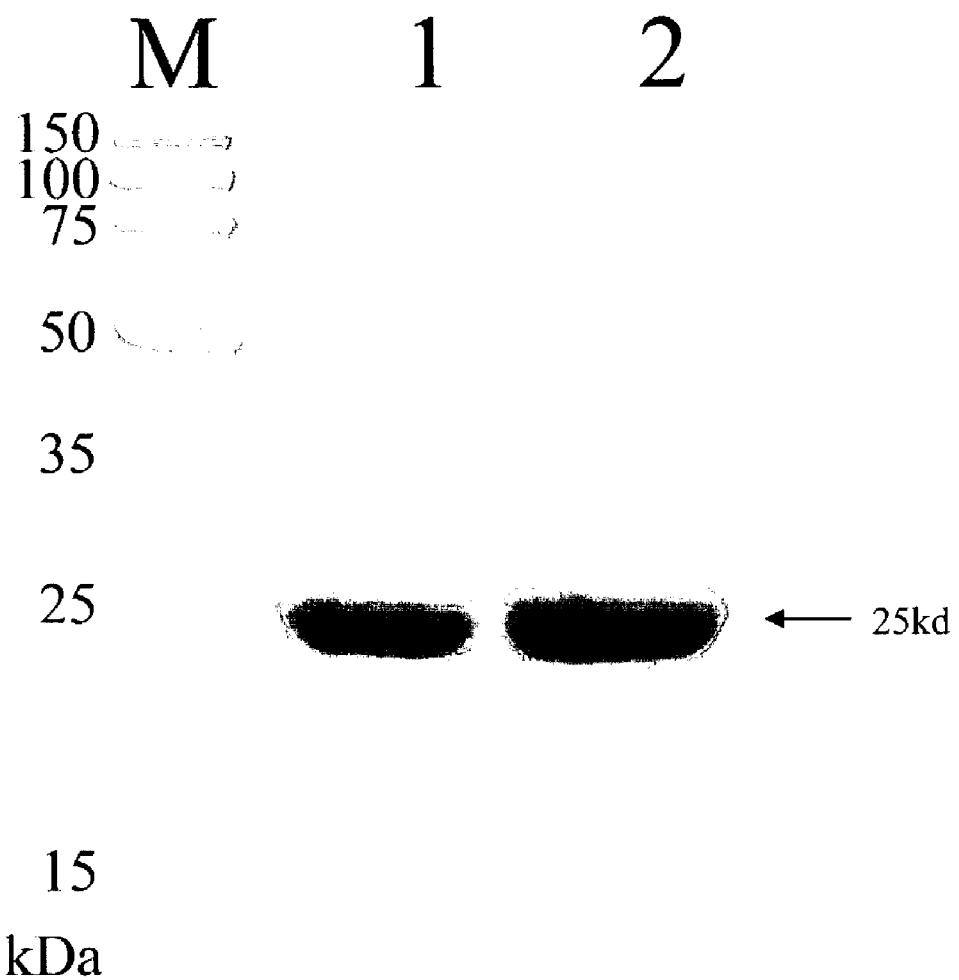
FIG. 5 represents a SDS-PAGE analysis for purified Thio/HTLV-I gp21 (lane 1) and Thio/HTLV-II gp21 (lane 2) fusion proteins (25 kDa).

The fusion protein Thio/HTLV-I/II gp21 was prepared for direct sandwich ELISA which reduces non-specific signals in background. The results of purified fusion protein Thio/HTLV-I/II gp21 are shown in FIG. 5, Thio/HTLV-I gp21 (lane 1) and Thio/HTLV-II gp21 (lane 2) are both 25 kDa and purity over 95%.

EXAMPLE 10

Biotinylatin of Antigenic Protein

GST/HTLV-I/II gp21 (33 kDa) was concentrated to 1 mg/mL and dialyzed to PBS buffer. Dissolved biotin protein solution was added to the protein solution slowly with continuous mixing. After a 2-hour reaction at 4° C., Tris HCl was added to a final concentration of 50 mM to terminate the reaction. The biotin-labeled protein was then dialyzed to 50 mM Tris HCl for the subsequent direct sandwich ELISA.

EXAMPLE 11

Assay of Specificity and Sensitivity for Human Sera

The preliminary test results show that Thio/HTLV-II gp21 can be used for coating in accompaniment with biotin-labeled GST/HTLV-I gp21. To investigate whether HTLV fusion protein has good sensitivity, HTLV sera standard control (Anti-HTLV I/II Mixed Titer Performance Panel, BBI) and sera from Tainan Blood Donation Center identified as positive by western blotting were used. Normal sera were used for testing specificity of the fusion protein. In the method described below, 1 μg Thio/HTLV-II gp21 per well diluted in 100 µl coating buffer (0.013M Na₂CO₃, 0.035M NaHCO₃, pH 9.6) was coated on 96-well plate. After 1 hour incubation at 37° C., the plate was washed with PBST (PBS with 0.05% Tween 20) three times. 200 µl overcoating buffer (GBC corp.) was added per well to incubate at 37° C. for 2 hours. The fluid was drawn out and the plate was stored at −20° C. for the subsequent experiment. 100 µl 20× diluted sample sera in 5H Specimen Diluent C (GBC corp.) was added per well and the plate was incubated at 37° C. for 1 hour. The plate was then washed with PBST six times. 100 µl 250× diluted biotin-labeled GST/HTLV-I gp21 in 2Ha conjugate Diluent (GBC corp.) was added per well and the plate was incubated at 37° C. for 1 hour. The plate was then washed with PBST six times. 100 µl Avidin conjugate AP (1:5000 dilution) in 2Ha conjugate Diluent (GBC corp.) was added per well and the plate was incubated at 37° C. for 1 hour. The plate was then washed with PBST six times. 5 mg p-nitrophenyl phosphate (Sigma) was dissolved in 5 ml color developing buffer (10% Diethanolamin, 0.5 mM MgCl₂) as color developing solution. 100 µl color developing solution was added per well and the plate was incubated at 37° C. for 15 min. The results were read at OD 405 nm by ELISA reader (Bio-Rad Model 550).

The results show that the average absorbance is 1.052 for sera from Taiwan Blood Donation Center identified as positive by western blotting (19 samples of HTLV-I positive), 1.098 for Anti-HTLV I/II Mixed Titer Performance Panel (BBI) (7 samples of HTLV-I positive and 11 samples of HTLV-II positive), 0.1528 for 92 normal sera. The results have significant differences between positive and negative samples. The fusion proteins have good sensitivity and specificity, with both exceeding 99%. Therefore, the fusion protein can act as a detection agent for HTLV.

While the invention has been particularly shown and described with the reference to the preferred embodiments thereof, it will be understood by those skilled in the art that various changes in form and details may be made without departing from the spirit and scope of the invention.

---

What is claimed is:

1. An isolated peptide wherein the peptide is (1) a fusion protein of glutathione S-transferase and an antigenic fragment of HTLV-I gp21, having the amino acid sequence of SEQ ID NO: 5; the peptide is (2) a fusion protein of thioredoxin and an antigenic fragment of HTLV-I gp21, having the amino acid sequence of SEQ ID NO: 7; the peptide is (3) a fusion protein of glutathione S-transferase and an antigenic fragment of HTLV-II gp21, having the amino acid sequence of SEQ ID NO: 6; or the peptide is (4) a fusion protein of thioredoxin and an antigenic fragment of HTLV-II gp21, having the amino acid sequence of SEQ ID NO: 8.

2. The isolated peptide of claim 1, wherein the peptide is a fusion protein of glutathione S-transferase and an antigenic fragment of HTLV-I gp21, having the amino acid sequence of SEQ ID NO: 5.

3. The isolated peptide of claim 1, wherein the peptide is a fusion protein of thioredoxin and an antigenic fragment of HTLV-I gp21, having the amino acid sequence of SEQ ID NO: 7.

4. The isolated peptide of claim 1, wherein the peptide is a fusion protein of glutathione S-transferase and an antigenic fragment of HTLV-II gp21, having the amino acid sequence of SEQ ID NO: 6.

5. The isolated peptide of claim 1, wherein the peptide is a fusion protein of thioredoxin and an antigenic fragment of HTLV-II gp21, having the amino acid sequence of SEQ ID NO: 8.

6. An expression vector, wherein the expression vector is deposited in the American Type Culture Collection and assigned (I) PTA-5238. (II) PTA-5240, (III) PTA-5239, or (IV) PTA-5241.

7. The expression vector of claim 6, wherein the expression vector is deposited in the American Type Culture Collection and assigned PTA-5238.

8. The expression vector of claim 6, wherein the expression vector is deposited m the American Type Culture Collection and assigned PTA-5240.

9. The expression vector of claim 6 wherein the expression vector is deposited in the American Type Culture Collection and assigned PTA-5239.

10. The expression vector of claim 6 wherein the expression vector is deposited in the American Type Culture Collection and assigned PTA-5241.

11. A kit for the detection of human T-lymphotropic virus (HTLV), comprising:
a solid substrate,
a first HTLV gp21 antigenic fragment immobilized on the solid substrate,
a blocking solution for blocking a HTLV gp21 antigenic fragment-unbound region on the solid substrate;
a second HTLV gp21 antigenic fragment,
a wash solution, and
a signal-producing means operably linked to the second HTLV gp21 antigenic fragment to produce a signal, wherein the first and the second HTLV gp21 antigenic fragments are different and are selected from;
(1) an isolated peptide consisting of a fusion protein of glutathione S-transferase and an antigenic fragment of HTLV-I gp21, with the amino acid sequence of SEQ ID NO: 5,
(2) an isolated peptide consisting of a fusion protein of thioredoxin and an antigenic fragment of HTLV-I gp21, with the amino acid sequence of SEQ ID NO: 7.
(3) an isolated peptide consisting of a fusion protein of glutathione S-transferase and the antigenic fragment of HTLV-II gp21, with the amino acid sequence of SEQ ID NO: 6, and
(4) an isolated peptide consisting of a fusion protein of thioredoxin and the antigenic fragment of HTLV-II gp21, with the amino acid sequence of SEQ ID NO: 8.

12. The kit as claimed in claim 11, wherein the first HTLV gp21 antigenic fragment is a first fusion protein of thioredoxin and the antigenic fragment of HTLV-II gp21, having the amino acid sequence of SEQ ID NO: 8; and the second HTLV gp21 antigenic fragment is a second fusion protein of glutathione S-transferase and the antigenic fragment of HTLV-I gp21, having the amino acid sequence of SEQ ID NO: 5.

* * * * *